(12) United States Patent
Ghiasvand et al.

(10) Patent No.: US 10,514,365 B2
(45) Date of Patent: Dec. 24, 2019

(54) COOLING-ASSISTED INSIDE NEEDLE CAPILLARY ADSORPTION TRAP DEVICE FOR ANALYZING COMPLEX SOLID SAMPLES USING NANO-SORBENT

(71) Applicants: Alireza Ghiasvand, Khorramabad (IR); Fatemeh Yazdankhah, Khorramabad (IR); Farzaneh Zarghami, Ahvaz (IR)

(72) Inventors: Alireza Ghiasvand, Khorramabad (IR); Fatemeh Yazdankhah, Khorramabad (IR); Farzaneh Zarghami, Ahvaz (IR)

( * ) Notice: Subject to any disclaimer, the term of this patent is extended or adjusted under 35 U.S.C. 154(b) by 170 days.

(21) Appl. No.: 15/276,400

(22) Filed: Sep. 26, 2016

(65) Prior Publication Data

US 2017/0059533 A1  Mar. 2, 2017

(30) Foreign Application Priority Data

Sep. 24, 2015 (IR) .................... 13945014000300717

(51) Int. Cl.
*G01N 1/22* (2006.01)
*B01J 20/281* (2006.01)
(Continued)

(52) U.S. Cl.
CPC .......... *G01N 30/482* (2013.01); *B01J 20/205* (2013.01); *B01J 20/262* (2013.01);
(Continued)

(58) Field of Classification Search
CPC .......... G01N 30/482; G01N 2030/484; G01N 2030/488; G01N 30/54; G01N 2030/025; G01N 2030/027; G01N 30/06; G01N 1/2294; G01N 2030/062; G01N 1/2214; G01N 33/24; G01N 2001/2229

USPC .......... 73/23.35–23.42, 31.07, 61.52–61.61, 73/64.56, 863.12; 210/656–659; 95/82, 95/87, 90–148; 96/101–107, 112, 96/143–146; 422/69, 70, 88, 89
See application file for complete search history.

(56) References Cited

U.S. PATENT DOCUMENTS 4,014,797 A  3/1977 Raines et al.
4,681,301 A  7/1987 Rinio
(Continued)

OTHER PUBLICATIONS

Non-Final Office Action Issued in U.S. Appl. No. 15/083,206, dated Mar. 22, 2018, 23 Pages.

*Primary Examiner* — Robert R Raevis
(74) *Attorney, Agent, or Firm* — NovoTechIP International PLLC

(57) ABSTRACT

A cooling-assisted inside needle capillary adsorption trap device for sampling and delivering volatile and semi-volatile analytes to an analytical device is disclosed. The device includes an inside needle capillary adsorption trap having a first end and a second end and a side aperture located between the first and second ends. The side aperture enables entering the carrier gas into the INCAT and flowing upon the surface of the sorbent (when injected into the GC injector) for complete releasing and eluting of the analytes from the interior surface of the needle. A sorbent is multiwall carbon nanotube/polyaniline and is coated onto the interior surface of the needle between the second end and the side aperture to entrap an analyte within a sample. The cooling-assisted inside needle capillary adsorption trap device also includes a cooling device configured to cool the sorbent.

11 Claims, 6 Drawing Sheets

(51) Int. Cl.
  *G01N 30/06* (2006.01)
  *B01J 20/26* (2006.01)
  *B01J 20/20* (2006.01)
  *G01N 30/00* (2006.01)
  *G01N 33/24* (2006.01)

(52) U.S. Cl.
  CPC ........... G01N 1/2294 (2013.01); G01N 30/06 (2013.01); *B01J 2220/46* (2013.01); *G01N 1/2214* (2013.01); *G01N 33/24* (2013.01); *G01N 2001/2229* (2013.01); *G01N 2030/062* (2013.01); *G01N 2030/484* (2013.01)

(56) References Cited

U.S. PATENT DOCUMENTS

| | | | | |
|---|---|---|---|---|
| 4,732,046 A | * | 3/1988 | Lawrence | G01N 1/4022 250/282 |
| 5,064,418 A | | 11/1991 | Cronin | |
| 6,164,144 A | * | 12/2000 | Berg | G01N 1/405 73/863.21 |
| 7,749,443 B2 | | 7/2010 | Land, III | |
| 8,191,435 B2 | * | 6/2012 | Grate | G01N 1/2214 73/863.21 |
| 2001/0032521 A1 | * | 10/2001 | Pawliszyn | G01N 1/2214 73/864.71 |
| 2007/0056360 A1 | | 3/2007 | Grant | |
| 2007/0113616 A1 | * | 5/2007 | Schilling | G01N 30/18 73/23.41 |
| 2009/0308811 A1 | | 12/2009 | Tepper | |
| 2013/0102460 A1 | * | 4/2013 | Ramaprabhu | B01J 20/20 502/402 |
| 2013/0233054 A1 | | 9/2013 | Oliphant et al. | |
| 2014/0318274 A1 | | 10/2014 | Zimmerman | |
| 2015/0233655 A1 | * | 8/2015 | Ghiasvand | F25D 3/10 165/61 |
| 2017/0023533 A1 | * | 1/2017 | Ghiasvand | G01N 30/12 |

* cited by examiner

COOLING-ASSISTED INSIDE NEEDLE CAPILLARY ADSORPTION TRAP DEVICE FOR ANALYZING COMPLEX SOLID SAMPLES USING NANO-SORBENT

CROSS REFERENCE TO RELATED APPLICATION

This application claims the benefit of priority to an Iran Application Serial Number 139450140003007175, filed on Sep. 24, 2015, entitled "A cooling-assisted inside needle capillary adsorption trap (CA-INCAT) device prepared by electrodeposition of nanoparticles for analyzing of volatile and semi-volatile analytes in complicated samples" and issued as Iran Patent Number 88478, the entire content of which is incorporated herein by reference.

TECHNICAL FIELD

This application relates generally to a Cooling-Assisted Inside Needle Capillary Adsorption Trap (CA-INCAT) for sampling that can be used to directly extract analytes from complicated solid samples and deliver them to a gas chromatography (GC) system. More specifically, the application discloses a cooling system to assist and enhance the extraction efficiency of the analytes.

BACKGROUND

Historically, the chief method of analyzing trace volatile chemicals (analytes), was solid-phase microextraction (SPME) which employs a fiber to collect the analyte and inject it into a gas chromatograph (GC) or liquid chromatograph (LC) system. This resulted in the capture and injection of only small quantities of the analytes and thus yielded poor sensitivity. It was discovered that if large quantities of vapor or liquid analyte were drawn through a treated sorbent, the components of interest would be concentrated. Solvents were used to selectively remove the analyte from the sorbent and a small portion of the solvent containing the analytes was then injected into the GC or LC. Concentration of the sample via a sorbent was an improvement in simplicity and sensitivity over straight analyte injection, but it added many processing steps to the analysis, which could increase errors.

Moreover, the environmental impact, chemical composition, concentration trends, and health effects of airborne particulate matter have been extensively studied and described in the literature. Current sampling methods involve the use of gravimetric filters or impact devices, and a wide variety of light and laser scattering devices. Many of the analytical methods for determination of chemical composition of airborne particulate matter require either sophisticated equipment and/or use strict sample preparation techniques. The task of sampling and analysis of airborne particulate matter is often complicated by the complexity of particle size, particle interactions, chemical partitioning between gaseous and particulate phase, and interactions with the sampling media. The health effects of inhaled particulate matter are associated with both the size and shape, as well as chemical toxicity. One of the better known groups of analytes from the latter category and also in soils and environmental waters are polycyclic aromatic hydrocarbons (PAHs).

Amongst pollutants, PAHs have received increased attention in recent years due to their suspected carcinogenic and/or mutagenic nature. PAHs originate in incomplete combustion, and are commonly found in gasoline and diesel motor exhaust, as by-products of open fires, industrial smoke, cigarette and cigar tobacco and smoke. Other sources include coal tar, coal tar pitch, wood preserving agents and coatings, mineral oils, and asphalt. Current most widely used sampling method, solid phase extraction (SPE), for PAHs involve the use of high-volume pumps, filters and sorbent cartridges. These methods require extraction from a filter (or sorbent) with an appropriate solvent, followed by subsequent analysis by HPLC with fluorescence or UV detection, or gas chromatography/mass spectrometry (GC/MS). Many of these methods require considerable sampling expertise and sophisticated equipment, long sample collection and preparation time, and strict extraction procedures. Thus, there is a growing demand for faster, simpler and cost-effective sampling for analytical methods for airborne, water and soil PAHs without compromising low detection limits achievable with some of the conventional methods. In addition, these new techniques should be reusable and environmentally friendly.

SUMMARY

The instant application describes a cooling-assisted inside needle capillary adsorption trap (CA-INCAT) system configured to sample and deliver analyte to an analytical device e.g. gas chromatograph (GC). Stainless steel needles, may size similarly to GC injection needles and packed with a sorbent bed, are used for extraction of samples, followed by thermal desorption into GC systems. All analytes, by heating the sample, are released from the soil sample and freely dissolved in the headspace gas and associated with matter entrained in the sample, may be extracted by the device.

The cooling-assisted inside needle capillary adsorption trap device may include an INCAT, a cooling system, a nano sorbent, a sample, an extraction vial, a heater, a liquid $CO_2$ tank, a solenoid valve, a temperature controller and a thermocouple.

The above general aspect may include one or more of the following features. A sorbent may be packed and placed between the working tip and the side aperture and may be configured to entrap the analyte within the sample received within the interior space of the needle.

The inside needle capillary adsorption trap device includes a first end and a second end. The first end, the syringe tip or the free end, may be configured to engage with a pump or syringe and the second end, the working tip, is configured to be inserted inside an extraction vial. The working tip may include an opening for receiving the sample within the body of the INCAT device. The INCAT device may be inserted into a cooling device on the working tip (out of extraction vial).

The INCAT device may include gauge 21 stainless-steel needle with a side hole and its internal surface coated by multi-wall carbon nanotube/polyaniline (MWCNT/PANI) nanocomposite. The MWCNT/PANI nanocomposite was synthesized via an electrochemical polymerization method on the interior wall of the INCAT device. First, aniline was dissolved in a sodium dodecyl sulfate electrolyte (SDS). Then 0.1 g MWCNT was added to the solution. The solution was used as the polymerization electrochemical solution. Two similar 21 G needles were used as anode and cathodes, respectively. A peristaltic pump was used to flow the solution through the needles. By applying a voltage equal to 1.4 V, the MWCNT/PANI was formed inside of the inside needle capillary adsorption trap device. To avoid losing the sorbent while operating, the needle was heat-treated in an oven for 1 hour at 280° C. under nitrogen atmosphere.

The additional details of the present application are set forth in the accompanying drawings and the description below. Once the details of the application are known, additional alternatives and changes will become obvious to one skilled in the art.

BRIEF DESCRIPTION OF THE DRAWINGS

Features of the subject technology are set forth in the appended claims. However, for purpose of explanation, several implementations of the subject technology are set forth in the following figures.

DETAILED DESCRIPTION

Figure 1:
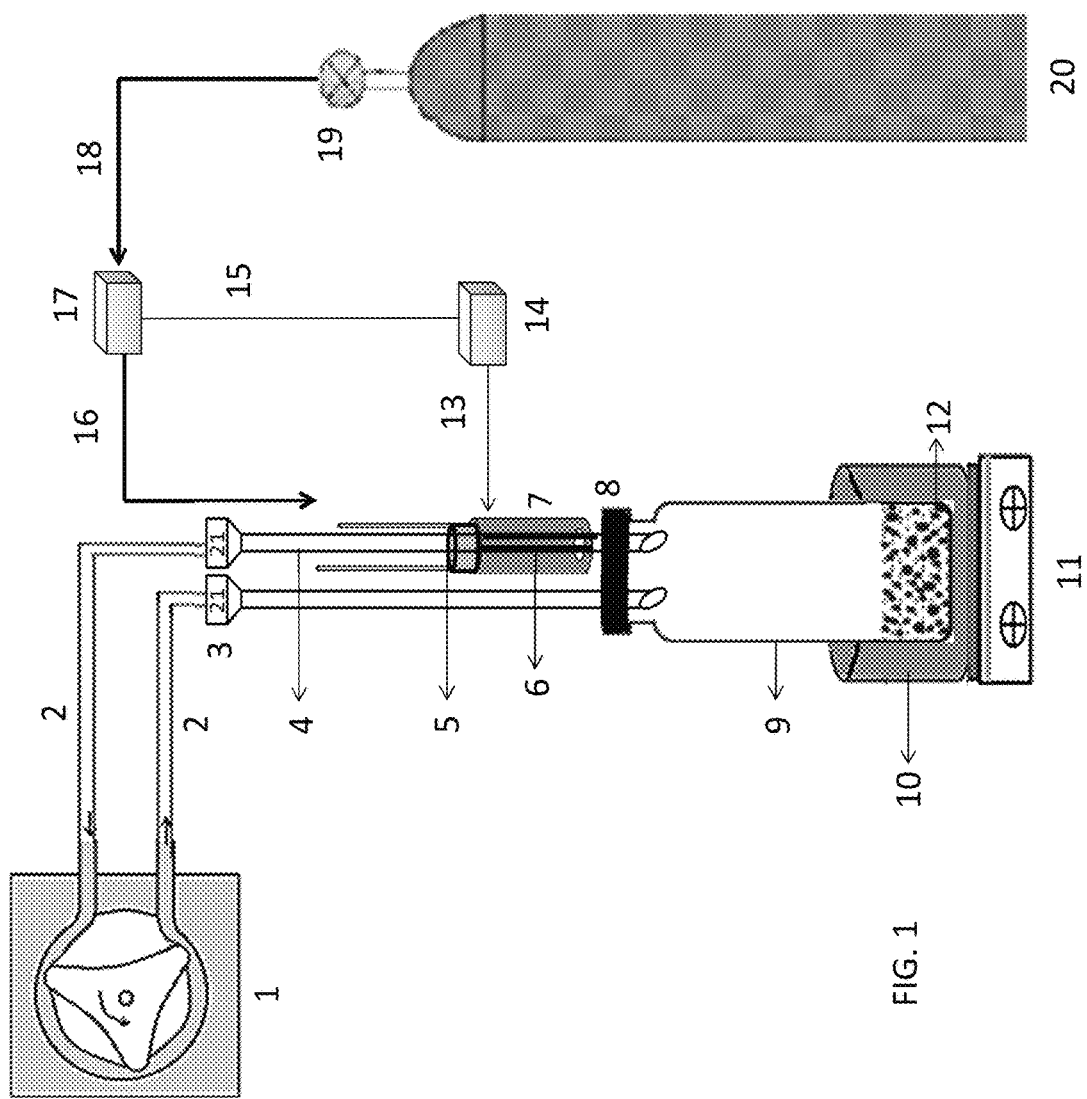
FIG. 1 illustrates a schematic of a cooling-assisted inside needle capillary adsorption trap (CA-INCAT) system according to one implementation of the instant application.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The instant application describes a cooling-assisted inside needle capillary adsorption trap system configured to sample and deliver analyte to an analytical device e.g. gas chromatograph. Stainless steel needles, may size similarly to gas chromatographic injection needles and packed with a sorbent bed, are used for extraction of samples, followed by thermal desorption into GC systems. All analytes, by heating the sample, are released from the soil sample and freely dissolved in the headspace gas and associated with matter entrained in the sample, may be extracted by the device.

In one implementation, the sorbent is coated into the interior surface of a needle between the working tip and a side hole. For desorption, the needle is inserted into the hot injector of gas chromatograph with a narrow-neck liner. The syringe tip seal against the carrier gas, however, the carrier gas is diverted into the needle through the side hole, subsequently passing the sorbent, and analytes are thermally desorbed and carried into the GC column. Inside needle capillary adsorption trap device may be used for either spot (grab) sampling or integrated (time-weighted sampling). For spot sampling a gas tight syringe or gas sampling pump may be connected to the free end of the needle and used to draw a pre-defined sample volume through the needle. The gas concentration is determined by determining the amount of analyte desorbed and dividing by the sample volume.

For integrated sampling, the syringe tip and side-hole are sealed and the open working tip of the needle is exposed to the sample for an extended period of time. The open working tip of the needle provides a suitable diffusion restriction to provide for analyte uptake rates proportional to sample concentration for several hours. The amount desorbed is thus related to the average sample concentration during the entire exposure time.

As for other gas sampling sorbent tubes, sampling rate and volume should be standardized and minimum breakthrough volume should be determined for the target sample during method development. Instrumentation to facilitate automated processing of needle trap device is commercially available for both desorption of multiple field-sampled needle trap device and automated extraction and desorption from sample vials. Automated processing also simplifies method development and the workstation is compatible with a variety of gas chromatographic instruments.

The inside needle capillary adsorption trap (INCAT) device may be more robust and cost-effective than solid-phase microextraction (SPME). The INCAT may also have a higher sorbent capacity, which makes it capable of performing exhaustive extraction. Depending on the concentration of analytes in the sample, the devices may be re-used from a few to dozens of times. To date INCAT has been used primarily for environmental analysis and breath analysis but is amenable to application for additional analytical chemistry applications. Sampling from headspace of water or solid samples by INCAT is a new and challenging topic in this area.

FIG. 1 illustrates a cooling-assisted inside needle capillary adsorption trap ("CA-INCAT") device in accordance with one implementation of the instant application. The ("CA-INCAT") device may include a peristaltic pump 1, a Teflon tube 2, a normal stainless steel needle 3, an INCAT stainless steel needle 4, a silicon septum 5, a thin layer of MWCNT-PANI composite nanosorbent 6, a cooling system 7, a plastic crimp cap 8, a standard SMPE sample vial 9, a sand-bath 10, an electric heater 11, a sample 12, a thermocouple 13, a temperature controller 14, a solenoid valve 15, a solenoid valve 17, a main fluid tank 18, a pressure regulator 19, and a fluid tank 20.

The peristaltic pump 1 may include FLEXIFLO ENTERNAL PUMP, Ross Products, Columbus, Ohio, USA, in one specific example. The Teflon tubes 2 are coupled to the peristaltic pump 1 and the needles 3 and 4 and are configured for circulation of the headspace of sample 12. The normal stainless steel needle 3 may be normal stainless steel needle (G21) only for allowing the circulation of the headspace inside the standard SMPE sample vial 9. The INCAT stainless steel needle 4 may be INCAT stainless steel needle (G21) with a side hole. The portion of the interior surface of needle 4 may be coated by PANI/MWCNT nanocomposite by electrodeposition method. The needle 4 includes a first end and a second end. The first end, the syringe tip or the free end, may be configured to engage with a pump 1 or syringe via Teflon tube 2 and the second end, the working tip, is configured to be inserted inside the headspace of an extraction vial 9. The extraction vial 9 may be 40 mL standard SPME sample vial from Supelco, in one specific example.

The extraction vial 9 may be placed inside a sand-bath 10 for uniform heating by an electric heater 11. The working tip of needle 4 may include an opening for receiving the headspace of sample 12 within the body of the CA-INCAT device. The CA-INCAT device may be covered by the cooling device 7 on the working tip needle 4. The cooling system 7 may be located on the lower side of the needle 4 and covers the part of needle 4, which contains the nanocomposite sorbent 6. The cooling system 7 includes two concentric copper tubes with first (outer tube) copper tube 2.5 cm in length and 0.9 cm and 1.0 cm in inner and outer diameters, respectively, and the second (inner tube) copper tube 2 cm in length and 0.5 cm and 0.6 cm in inner and outer diameters, respectively. The second tube is placed within the first tube. The concentric tubes thereby make a jacket with a hollow cylindrical space between the tubes that provides the path for the coolant fluid.

In order for the coolant fluid to enter and exit the cooling device 7, which includes the cylindrical hollow space between the concentric tubes, there are two side holes on the outer tube. The cooling process takes place between the concentric tubes. The coolant enters the first hole, flows on the surface of the inner tube and cools down the sorbent 6 which is covered by the inner tube. The first side hole, near one end of the outer tube, is attached to a 5 cm-long stainless steel capillary tube and used as the inlet channel for the coolant fluid. Another side hole on the outer tube, and near the other end of the outer tube, is attached to a 7 cm-long stainless steel capillary tube as the outlet channel for the coolant fluid. Choosing difference-sized capillary tubes may be for inducing a pressure difference inside the cooling device to enhance the efficiency of the liquid $CO_2$ expansion and consequently cooling process. A silicon septum 5 seals the cooling system's end 7 to prevent gas leakage. A plastic crimp cap 8 coats the silicon septum 5.

A fluid tank 20 is attached to the cooling system 7 to store the coolant fluid. Stainless steel tubes for entering of liquid CO2 and exiting of CO2 gas from the cooling capsule (the entrance tube was 19XX-G, located near the bottom of the inter-walls space of the copper tubes and the exit tube was 22XX-G, located near the top of it). A thermocouple 13 is attached to the outside of the outer concentric tube and coupled to the temperature controller 14. The thermocouple 13 measures the temperature inside the cooling device 7 and sends it to the temperature controller 14. The thermocouple 13 may be fixed onto the surface of cooling system 7 using an insulating Teflon cover (in addition to fixing of thermocouple, the cover prevents cold's loss).

The temperature controller 14 is connected to the thermocouple 13 and equipped with a logic circuit and suitable software to record temperature data at preset intervals.

The cooling device 7 covers the sorbent 6, which is located inside the working tip of the inside needle capillary adsorption trap device. The sorbent 6 adsorbs the analyte from the sample 12. The sample 12 may be soil sample which is directly poured into the sample vial 9 and analyzed without any pretreatment step. Wires 15 connecting the temperature controller 14 to the solenoid valve 17 turn off/on the solenoid valve 17 based on the preset program of the temperature controller 14 which is equipped with a logic circuit and a software to record temperature at preset intervals. The solenoid valve 17 may be 220 VAC/50/60 HZ, 0.25 bar/Class E, Mahar Fan Abzar Co., Tehran, Iran, in one specific example.

The controller 14 is configured to control the coolant fluid flow through the solenoid valve 17 (0.25 bar/class E, 50/60 Hz, 220V AC, G1/8). The coolant fluid flows through a stainless steel tube 16 form the solenoid valve 17 to the entrance of the cooling device 7. Another stainless steel tube 18 delivers the coolant fluid from the fluid tank 20 to the solenoid valve 17. The pressure of the fluid is controlled by a pressure regulator and valve 19 on the fluid tank 20.

The sample 12 is placed in an extraction vial 9. In the extraction vial 9 the sample 12 will be heated by a sand-bath 10 around the sample vial 9 and on top of a heater 11 to enhance the extraction of the analyte. The heater 11 may be electric hotplate (Heidolph, Germany), in one specific example.

The released analyte from the sample matrix then enters the working tip of the inside needle capillary adsorption trap device (by circulation through a peristaltic pump 1), where it is adsorbed by the nanosorbent 6. Since adsorption of the analyte to the surface of the nanosorbent 6 is exothermic in nature, the nanosorbent 6 section of the inside needle capillary adsorption trap device may be cooled by the cooling system 7 to enhance the efficiency of the adsorption process. A peristaltic pump 1 attached to the syringe tip of the inside needle capillary adsorption trap device may be used for suctioning the headspace and then returning sample in the headspace to the extraction vial 9 for exhaustive adsorption of entire analyte. The extraction process is assisted by cooling down the nanosorbent 6 temperature to increase the adsorption efficiency of the nanosorbent 6 via a cooling system 7. The extraction vial 9 may be covered by cap 8. The cap 8 may be plastic crimp cap with a PTFE-coated silicone septum.

Figure 2:
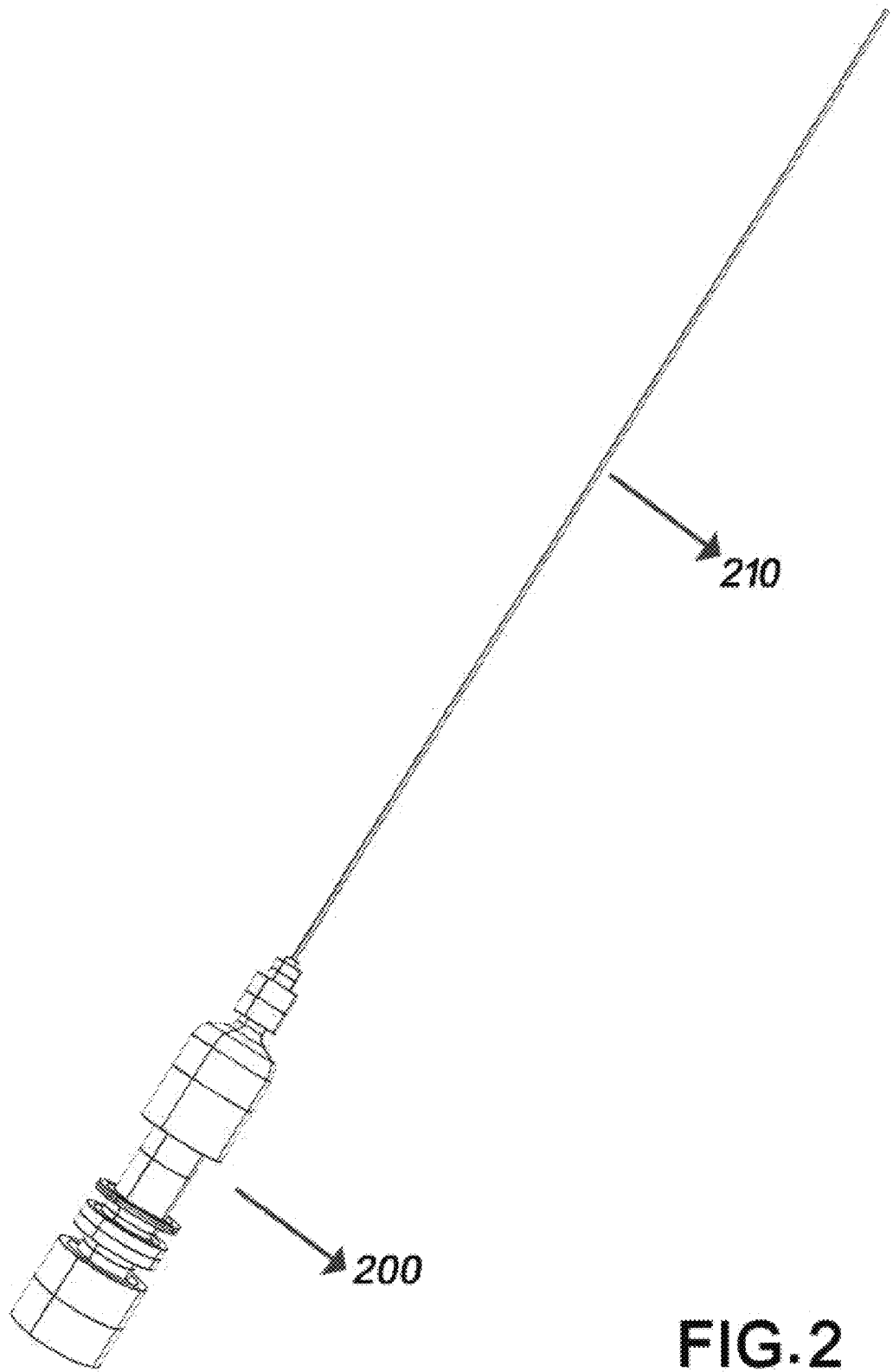
FIG. 2 illustrates an exemplary inside needle capillary adsorption trap (INCAT) device with a side hole according to one implementation of the instant application.

FIG. 2 illustrates an exemplary inside needle capillary adsorption trap device 200. The inside needle capillary adsorption trap device 200 includes a working tip 210, a syringe tip, a side hole, and a sorbent thin layer covered inside the inside needle capillary adsorption trap device 200 between the working end 210 and the side hole. The working tip of the inside needle capillary adsorption trap device 200 surrounded by the cooling system is positioned inside an extraction vial. Upon heating the sample by the heater below the extraction vial, the analyte releases from the sample and enters the working end of the inside needle capillary adsorption trap device 200 where it adsorbs on the nanosorbent surface. The un-adsorbed part of the analyte may be sucked by the peristaltic pump and be returned to the extraction vial for further extraction. Unlike the conventional methods where some sample preparation step is required to extract the analytes, the needle trap device is introduced into a conventional GC injector for sample desorption without further preparation steps. The advantages of such a system are many, e.g., the extraction trap device may not require sample pretreatment and solvents involved and the total sampling and analysis time may be relatively short and significantly reduced when compared to many existing methods. As such, it can serve as a screening tool, wherever fast analysis is needed. In addition, such a device can also serve as a time-weighted average sampler, where either continuous sampling over long sampling time or a sequence of short sampling events within a required sampling period is used.

Figure 3:
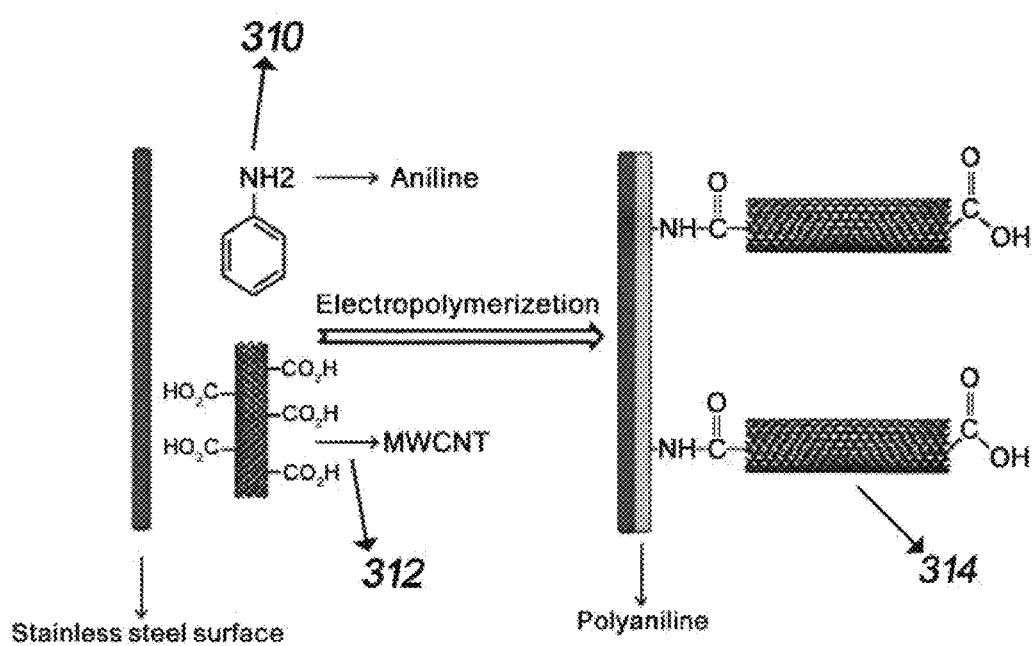
FIG. 3 illustrates the synthesizing, electropolymerization and electrodeposition process of the sorbent.

FIG. 3 illustrates the synthesizing process 300 of the sorbent. On the left side, the stainless steel tube as the electrodes and the reactant, aniline 310 and multiwall carbon nanotube 312 are shown. The inside needle capillary adsorption trap device may include gauge 21 stainless-steel needle with a side hole packed with multi-wall carbon nanotube/polyaniline-composite (MWCNT/PANI). The multi-wall carbon nanotube/polyaniline-composite (MWCNT/PANI) was synthesized via an electrochemical polymerization method on the interior wall of the inside needle capillary adsorption trap device. First, aniline 310 was dissolved in a sodium dodecyl sulfate electrolyte (not shown). Then 0.1 g multi-wall carbon nanotube 312 was added to the solution. The solution was used as the polymerization electrochemical solution. Two similar 21 G needles were used as anode and cathodes, respectively. A peristaltic pump was used to flow the solution. By applying a voltage equal to 1.4 v, the MWCNT/PANI 314 was formed inside of the inside needle capillary adsorption trap device. To avoid losing the sorbent while operating, the needle was heat-treated in an oven for 1 hour at 280° C. under nitrogen atmosphere.

Figure 4:
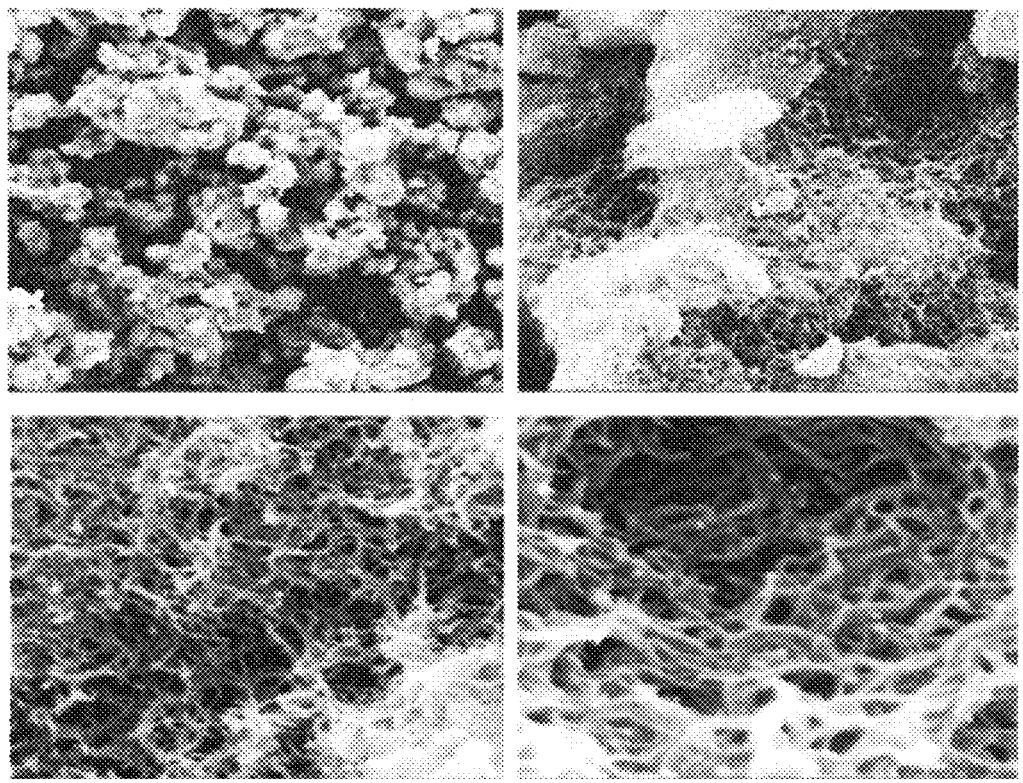
FIG. 4 illustrates scanning electron microscopy (SEM) images of the synthesized multi-wall carbon nanotube/polyaniline-composite (MWCNT/PANI) nanocomposites.
Figure 5:
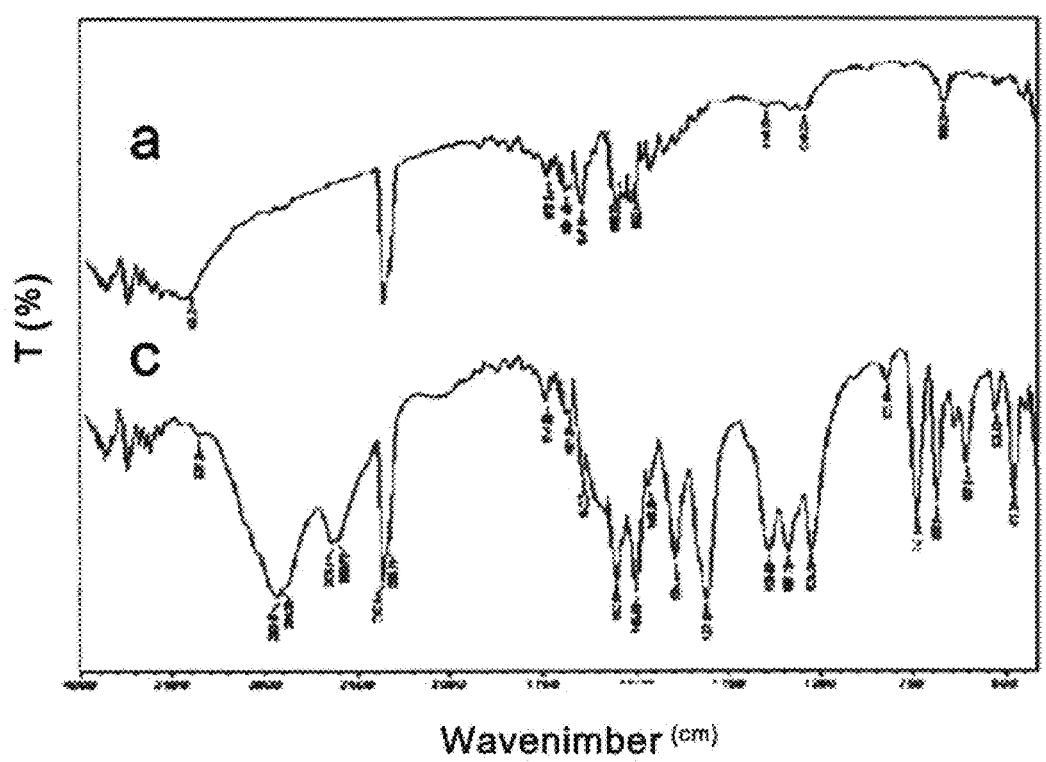
FIG. 5 shows the FT-IR spectrum of a) the synthesized multi-wall carbon nanotube (MWCNT) and b) multi-wall carbon nanotube/polyaniline-composite (MWCNT/PANI) nanocomposite.

FIG. 4 illustrates scanning electron microscopy (SEM) images of the synthesized multi-wall carbon nanotube/polyaniline-composite (MWCNT/PANI) nano-composites. FIG. 5 also shows the FT-IR spectrum of the synthesized multi-wall carbon nanotube (a) and multi-wall carbon nanotube/polyaniline-composite (MWCNT/PANI) nanocomposites (b).

Figure 6:
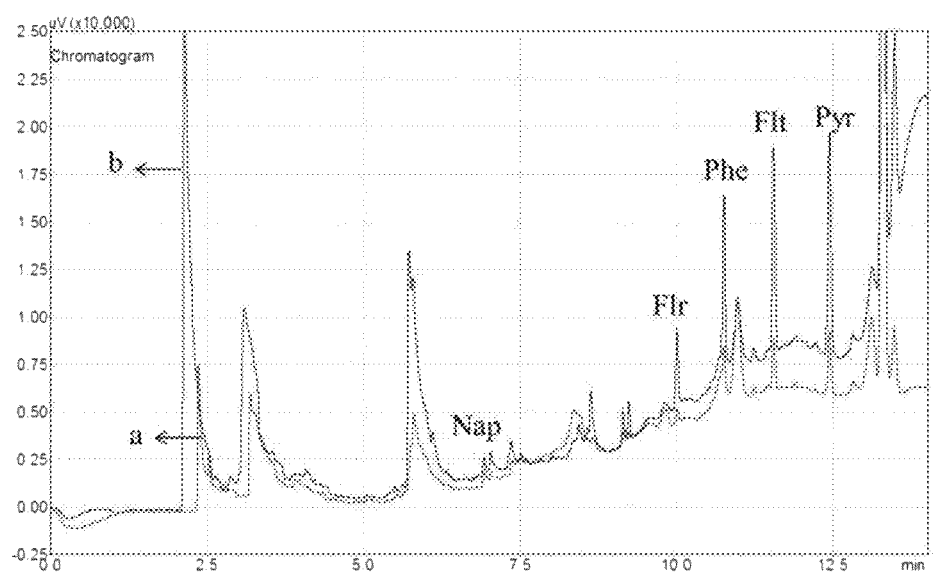
FIG. 6 shows GC-FID chromatogram of the PAHs extracted using CA-INCAT method a) spiked soil real sample (b) unspiked soil real sample.

FIG. 6 shows a GC-FID chromatogram of the PAHs extracted from a contaminated soil sample which was carried out by the CA-INCAT of the present application. The extraction temperature was 120° C., extraction duration 15 min, needle temperature 0° C., sampling flow rate with pump 6.25 mL/min, humidity 30 µL $H_2O$/10 g sample, desorption time 4 min, and the desorption temperature 280° C. The Limit of Detection (LOD) of 5 PAHs was 0.00001-0.001 µg/g and the Relative Standard Deviation (RSD) was 7.7%-41.0%.

To cool the sorbent, liquid carbon dioxide may be used. A 10 L liquid tank is connected to the cooling device through a solenoid valve which controls the fluid flow. A thermocouple attached to the surface of the outer tube of cooling device, measures the temperature of the sorbent and a temperature controller controls the solenoid valve state. When the temperature exceeds a pre-determined threshold, the temperature controller instructs the solenoid valve to open further. The temperature controller closes the solenoid valve when the temperature inside the inside needle capillary adsorption trap device becomes less than a pre-determined threshold.

In one implementation, after extracting the analyte on the sorbent, the inside needle capillary adsorption trap device may be detached from the extraction vial injected into the injection port of a chromatograph e.g. GC-FID to separate and measure the analyte quantitatively. The free end of the needle may be sealed by silicon septum to avoid the carrier gas from purging.

The separation of various components in the examples described above should not be understood as requiring such separation in all examples, and it should be understood that the described components and systems can generally be integrated together in a single packaged into multiple systems.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations for the purpose of streamlining the disclosure. This method of disclosure is not to be interpreted as reflecting an intention that the claimed implementations require more features than are expressly recited in each claim. Rather, as the following claims reflect, inventive subject matter lies in less than all features of a single disclosed implementation. Thus the following claims are hereby incorporated into the Detailed Description, with each claim standing on its own as a separately claimed subject matter.

What is claimed is:

1. A cooling-assisted inside needle capillary adsorption trap system comprising:
    a needle including a first end and a second end and a side aperture positioned between the first end and the second end, and the side aperture being configured to enter a carrier gas into an interior surface of the needle INCAT for complete releasing and eluting of the analytes from the interior surface of the needle;
    a MWCNT/PANI nanocomposite sorbent included inside the interior surface of the needle between the second end and the side aperture and configured to entrap the analytes within a sample received within the interior space of the needle; and
    a cooling device configured to cool the sorbent and includes an inner tube and an outer tube, the outer tube having a diameter larger than the inner tube and including a first aperture and a second aperture;

a first capillary tube coupled to the first aperture and configured to be an inlet channel for a coolant fluid for cooling the sorbent; and a second capillary tube coupled to the second aperture and configured to be an outlet channel for the coolant fluid, wherein the inner tube is approximately 2.5 cm in length and 0.5 cm and 0.6 cm in inner and outer diameters, respectively, and the outer is approximately 2 cm in length and 0.8 cm and 1.0 cm in inner and outer diameter respectively.

2. The system of claim 1, further comprising:

a $CO_2$ fluid tank coupled to the first capillary tube and configured to store the coolant fluid;

a solenoid valve coupled to the first capillary tube on a pathway of the coolant fluid from the fluid tank to the first capillary tube and configured to control a flow of the coolant fluid flow;

a thermocouple coupled to the outer tube of cooling capsule to measure temperature of the cooling device; and a temperature controller configured to control an operation of the solenoid valve based on the temperature measured by the thermocouple.

3. The system of claim 2, further comprising:

an extraction vial configured to hold the sample and receive the second end of the needle from an opening in a top portion of the extraction vial; and a sand-bath on the top of a heating device placed around the extraction vial and configured to heat the sample.

4. The system of claim 1, wherein a peristaltic pump coupled to the first end of the needle is configured to circulate an analyte for adsorbing on to the sorbent in the interior surface of the needle.

5. The system of claim 1, wherein the needle is made of stainless steel.

6. The system of claim 1, wherein the needle is approximately 21-G in diameter.

7. The system of claim 1, wherein the sorbent is multiwall carbon nanotube/polyaniline-composite.

8. The sorbent of the claim 7, wherein the sorbent was made by a 2-electrode electrochemical polymerization technique.

9. The sorbent of the claim 8, wherein an electrolyte is a mixture of multiwall carbon nanotube and aniline in sodium dodecyl sulfate.

10. The system of claim 1, wherein the capillary tubes are made of stainless steel, wherein the first tube, the coolant fluid inlet, is approximately 5 cm in length and the second tube, the coolant fluid outlet, is 7 cm in length.

11. The system of claim 1, wherein the coolant fluid is liquid carbon dioxide.

* * * * *